United States Patent
Tong

(10) Patent No.: US 6,454,995 B1
(45) Date of Patent: Sep. 24, 2002

(54) PHOSPHINE COKE INHIBITORS FOR EDC-VCM FURNACES

(75) Inventor: Youdong Tong, Houston, TX (US)

(73) Assignee: Ondeo Nalco Energy Services, L.P., Sugar Land, TX (US)

( * ) Notice: Subject to any disclaimer, the term of this patent is extended or adjusted under 35 U.S.C. 154(b) by 109 days.

(21) Appl. No.: 09/638,426

(22) Filed: Aug. 14, 2000

(51) Int. Cl.⁷ .................................................. C23F 11/02
(52) U.S. Cl. ........................ 422/9; 208/48 AA; 585/950
(58) Field of Search ............... 422/7, 9; 208/48 AA, 208/106; 585/950; 526/318.25; 525/331.5

(56) References Cited

U.S. PATENT DOCUMENTS

| | | |
|---|---|---|
| 3,647,677 A | 3/1972 | Wolff et al. |
| 3,896,182 A | 7/1975 | Young |
| 4,551,227 A | 11/1985 | Porter et al. |
| 4,835,332 A * | 5/1989 | Kisalus |
| 5,354,450 A | 10/1994 | Tong et al. |
| 5,733,438 A | 3/1998 | Tong et al. |
| 5,779,881 A | 7/1998 | Tong et al. |
| 5,954,943 A | 9/1999 | Tong et al. |

FOREIGN PATENT DOCUMENTS

GB 1494797 12/1977

OTHER PUBLICATIONS

Sotowa, C et al. Abstract of Coking phenomena in the pyrolisis of ethylene dichloride into vinil chloride, Book of Abstracts, 210$^{th}$ ACS National Meeting, Chicago, IL, Aug. 20–24 (1995), Issue Pt. 2, PETR–095.

* cited by examiner

*Primary Examiner*—Elizabeth McKane
(74) *Attorney, Agent, or Firm*—Margaret M. Brumm; Thomas M. Breininger

(57) ABSTRACT

A method of reducing the formation of coke deposits on the heat-transfer surfaces of an ethylene dichloride to vinyl chloride pyrolysis furnace comprising exposing the heat transfer surfaces of said pyrolysis furnace to a phosphine selected from the group consisting of phosphines with the general formula:

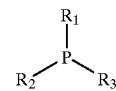

wherein $R_1$, $R_2$ and $R_3$ are selected from the group consisting of hydrogen, chlorine, alkyl, aryl, alkylaryl and arylalkyl, wherein $R_1$, $R_2$ and $R_3$ can be the same or different.

10 Claims, 3 Drawing Sheets

PHOSPHINE COKE INHIBITORS FOR EDC-VCM FURNACES

FIELD OF THE INVENTION

This invention relates to a method of inhibiting coke formation in pyrolysis furnaces. Specifically, this invention relates to a method of inhibiting coke formation in ethylene dichloride/vinyl chloride pyrolysis furnaces.

BACKGROUND OF THE INVENTION

Thermal pyrolysis or cracking of ethylene dichloride (EDC) to vinyl chloride (VC) is the major industrial process for vinyl chloride monomer (VCM) production at present. The thermal pyrolysis process entails the use of pyrolysis furnaces, also known as EDC-VCM furnaces, to thermally convert EDC to VC. The pyrolysis process occurs as a homogeneous, first-order, free-radical chain reaction. The general reaction mechanism involves the following steps:

Initiation: $ClCH_2CH_2Cl \rightarrow ClCH_2CH^{2\cdot} + Cl^{\cdot}$

Propagation: $Cl^{\cdot} + ClCH_2CH_2Cl \rightarrow ClCHCH_2Cl + HCl$
$ClCHCH_2Cl \rightarrow ClCHCH_2 + Cl^{\cdot}$ Termination: $Cl^{\cdot} + ClCH_2CH_2 \cdot \rightarrow ClCHCH_2 + HCl$ A typical pyrolysis furnace has three sequential building blocks: convection section, radiant section, and transfer line exchanger (TLE). Metal alloy serpentine coils run through the convection section and the radiant sections, and connect to the TLE. The convection section utilizes the convection heat from the radiant section to preheat, and sometime to vaporize and preheat EDC feed. The coils in the radiant section function as the pyrolysis reactor where the preheated EDC feed is cracked to VC.

Because of the severe operation environment in the pyrolysis furnaces, iron alloys of high Ni and Cr content are common materials of construction of the pyrolysis furnaces. The TLE is a heat exchange device, which quickly quenches the effluent from the pyrolysis reactor. The quenching is to stop any product degradation under adiabatic condition in the past furnace zone.

Industrial pyrolysis reactors are typically operated at temperatures of from about 470° C. to about 550° C. (about 878° F. to 1022° F.), at gauge pressures of from about 1.4 Mpa to about 3.0 Mpa (about 200 psig to about 435 psig) and with a residence time from about 2 seconds to about 30 seconds. EDC conversion per pass through a pyrolysis furnace is normally maintained around 50–55% with a selectivity of 96–99% to vinyl product. VC and HCl are the major components in the pyrolysis reactor effluent. By-products from the pyrolysis process range from the very lights, such as methane, acetylene, ethylene and methyl chloride, to the heavies, such as carbon tetrachloride, trichloroethane and solid carbonaceous material. Solid carbonaceous material is usually referred to as coke, and coke is an unwanted by product of the pyrolysis process.

Higher conversion in the pyrolysis process is, in most cases, desired. However, increasing cracking severity beyond conventional operation conditions generally leads to only a small increase in EDC conversion at the expense of the selectivity to vinyl chloride product. Furthermore, any outstanding increase in cracking severity causes a drastic increase in coke formation and a sharp drop in VC selectivity.

Fouling of the pyrolysis furnace occurs due to formation of coke. In fact, coke formation often becomes the major limitation in pyrolysis furnace operation and VC production. Formation of coke with resultant fouling decreases the effective cross-sectional area of the process feed flow through the pyrolysis furnace and the TLE, and thus increases the pressure drop across pyrolysis furnaces. In order to compensate for the pressure buildup, generally, a reduction in EDC feed rate is necessary. A reduction in EDC feed rate means an overall reduction in production. Another undesirable feature of coke formation is that the coke is a good thermal insulator, and thus coke formation reduces the heat transfer across the walls of the pyrolysis reactor. The reduction in heat transfer requires a gradual increase in furnace firing duty to maintain the cracking reactions at a desired conversion level. Furnace fire duty thus can also become the limiting factor for conversion and overall VC production. To maintain the capacity and the fire efficiency of pyrolysis furnaces at optimum levels, pyrolysis operation has to periodically cease for coke removal (decoke), which causes production down time.

Known methods for the removal of coke from pyrolysis furnaces include controlled combustion or mechanical cleaning, or a combination of both methods. In the combustion process, a mixture of steam and air of various steam/air ratios is admitted in the pyrolysis furnace at an elevated temperature, and the coke in the reactor is burnt out under a controlled condition. This process is conventionally referred as hot decoke. For the mechanical cleaning, coke is physically chipped off the pyrolysis furnace inner surface and removed from the reactor. Both cracking and the hot decoke operations expose the pyrolysis furnace to a cycle between a HCl and chlorinated hydrocarbon-rich reducing environment and an oxygen-rich oxidizing environment at elevated temperatures, which causes corrosion and degradation of the pyrolysis furnace and shortens the reactor lifetime. Therefore, methods of prevention of coke formation are desired in order to improve Vinyl chloride production and avoid the coke removal operation.

Great Britain Patent No. 1,494,797, VINYL CHLORIDE BY A DEHYDROCHLORINATION PROCESS, teaches a method of addition of 200–5000 PPM of 1,1,2-trichloroethane to reduce coke formation in EDC-VCM pyrolysis furnaces.

U.S. Pat. No. 3,896,182 teaches a method of reducing coke formation and fouling by lowering the oxygen content in the EDC feed.

Coke formation in pyrolysis furnaces continues to be undesirable and thus effective alternative methods to reduce the formation of coke in pyrolysis furnaces are always desired.

SUMMARY OF THE INVENTION

A method of reducing the formation of coke deposits on the heat-transfer surfaces of an ethylene dichloride to vinyl chloride pyrolysis furnace comprising exposing the heat transfer surfaces of said pyrolysis furnace to a phosphine selected from the group consisting of phosphines with the general formula:

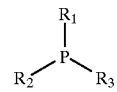

wherein $R_1$, $R_2$ and $R_3$ are selected from the group consisting of hydrogen, chlorine, alkyl, aryl, alkylaryl and arylalkyl, wherein $R_1$, $R_2$ and $R_3$ can be the same or different.

DETAILED DESCRIPTION OF THE INVENTION

Figure 1:
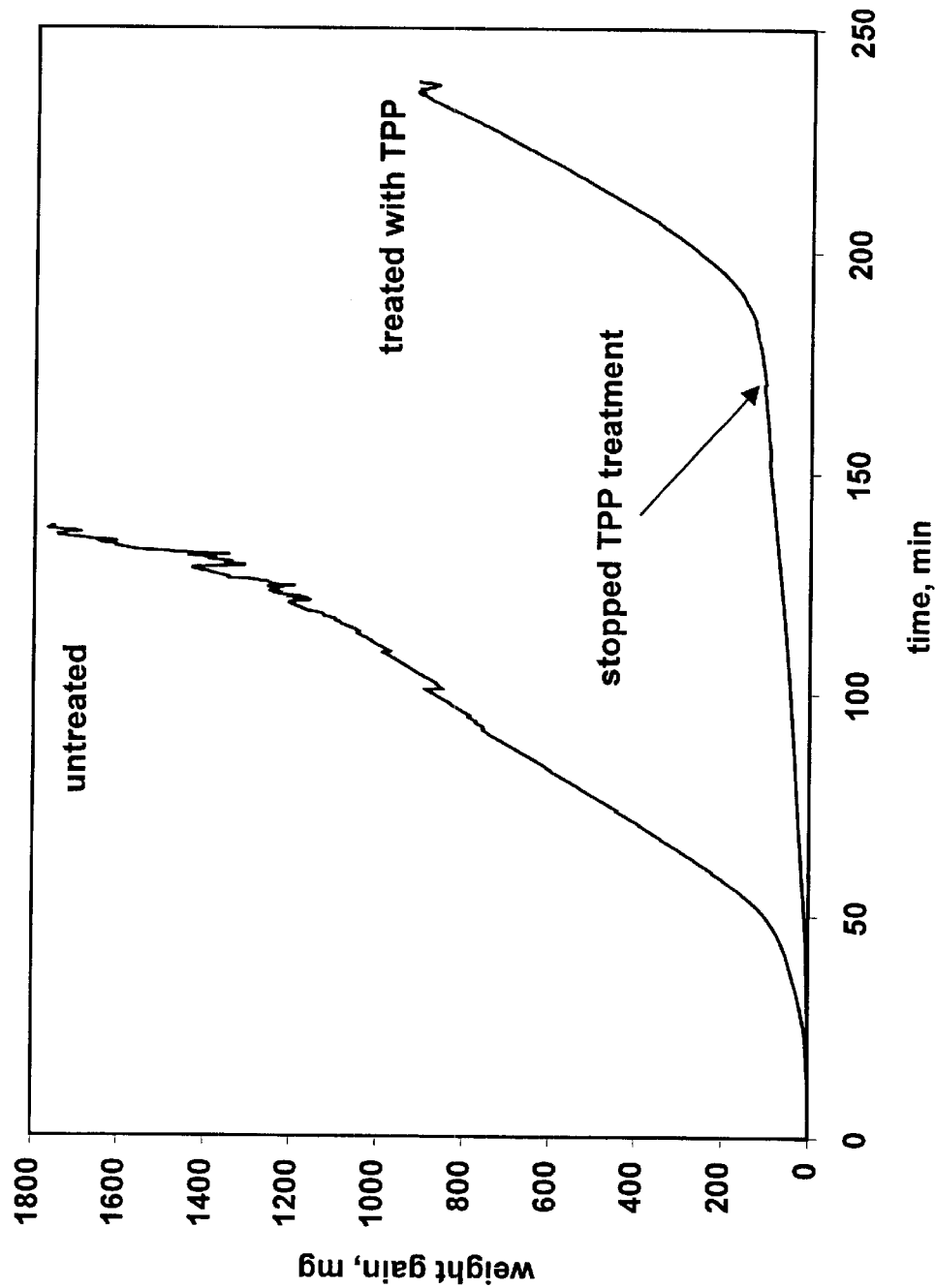
FIG. 1 is a graph illustrating the effectiveness of triphenyl phosphine (TPP) in inhibiting coke formation in comparison with an untreated run.

The following terms have the indicated meanings:

Coke means the solid carbonaceous material that is an unwanted by product of the pyrolysis reaction, Decoke means the removal of coke from a pyrolysis furnace, EDC means ethylene dichloride, which is also known as dichloroethane, EDC-VCM furnaces refers to ethylene dichloride to vinyl chloride pyrolysis furnaces, $PH_3$ is known as phosphorus hydride, TLE refers to transfer line exchanger.

VC means vinyl chloride,

VCM means vinyl chloride monomer.

The instant claimed invention is a method of reducing the formation of coke deposits on the heat transfer surfaces of an ethylene dichloride to vinyl chloride pyrolysis furnace comprising exposing the heat transfer surfaces of said pyrolysis furnace to a phosphine selected from the group consisting of phosphines with the general formula:

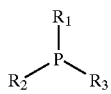

wherein $R_1$, $R_2$ and $R_3$ are selected from the group consisting of hydrogen, chlorine, alkyl, aryl, alkylaryl and arylalkyl, wherein $R_1$, $R_2$ and $R_3$ can be the same or different. For purposes of this patent application, "alkyl" means a fully saturated hydrocarbon moiety of from about 1 to about 40 carbon atoms. The alkyl moiety may optionally be substituted with one or more —Cl, —Br, —$SO_3$, —$OR_a$, —$SR_a$, —$NR_aR_b$, —$SiR_aR_bR_c$, and —$BR_aR_b$ groups, where $R_a$, $R_b$, and $R_c$ are selected from the group consisting of hydrogen, unsubstituted alkyl, unsubstituted aryl, unsubstituted alkylaryl and unsubstituted arylalkyl. The alkyl moiety is connected to the phosphorus atom through a bond to a carbon atom.

For purposes of this patent application, "aryl" means an aromatic monocyclic or multicyclic ring system radical of about 6 to about 20 carbon atoms. Preferably aryl is phenyl or naphthyl or anthracenyl. The aryl moiety is optionally substituted with one or more alkyl, alkenyl, —Cl, —Br, —$SO_3$, —$OR_a$, —$SR_a$, —$NR_aR_b$, —$SiR_aR_bR_c$, and $BR_aR_b$ groups, where $R_a$, $R_b$, and $R_c$ are selected from the group consisting of hydrogen, unsubstituted alkyl, unsubstituted aryl, unsubstituted alkylaryl and unsubstituted arylalkyl. The aryl moiety is attached to the phosphorous atom by a bond to one of the carbons in the ring.

For purposes of this patent application, "alkylaryl" refers to an aryl moiety with at least one alkyl substituent. The alkylaryl moiety is attached to the phosphorus atom by a bond to one of the carbons in the ring of the aryl portion of the alkylaryl moiety.

For purposes of this patent application, "arylalkyl" refers to an alkyl moiety with at least one aryl substituent. The arylalkyl moiety is attached to the phosphorus atom by a bond to one of the carbons in the alkyl portion of the arylalkyl moiety.

For purposes of this patent application, "alkenyl" refers to an unsaturated hydrocarbon radical of from about 2 to about 10 carbon atoms. Alkenyl moieties have one double bond. Preferably alkenyl is allyl.

The preferred phosphine compounds are those in which $R_1$, $R_2$ and $R_3$ are all the same.

Suitable phosphine compounds for use in the method of the instant claimed invention are phosphorous trichloride ($PCl_3$), triphenyl phosphine, tri-n-butyl phosphine, tri-n-octyl phosphine, tridodecyl phosphine, tricyclohexyl phosphine, tribenzyl phosphine, triphenyl phosphine, tris(p-tolyl)phosphine, tris(1-naphthyl)phosphine, tris(anthracenyl)phosphine, tris(3-chlorophenyl)phosphine and tris(2-methoxyphenyl)phosphine.

The phosphine compounds useful in the method of the instant claimed invention are either available commercially or can readily be synthesized using techniques known to ordinary people skilled in the art of phosphine compounds.

These phosphine compounds can be applied individually or they can be applied by mixing one or more of them together.

When being used in the method of the instant claimed invention, the phosphine can be used as neat (pure compound) or it can be blended with solvents or conversion boosters or a mixture of solvents and conversion boosters. Solvents for phosphines and conversion boosters for the EDC to VCM reaction are known in the art of phosphine chemistry and in the art of EDC to VCM chemistry.

The phosphine can be applied in different ways. The pyrolysis furnace can be contacted with phosphine prior to ethylene dichloride feed; this is known as pretreatment. Alternatively, or in conjunction with pretreatment, the pyrolysis furnace may be continuously or intermittently treated with phosphine during processing of EDC feed. This is known as continuous or intermittent treatment, respectively.

For pretreatment, the phosphine can be applied by using any of the following methods, including, but not limited to, spraying, soaking, painting, flushing and chemical vapor deposition. All of these methods are useful in conducting the method of the instant claimed invention, as long as they provide an effect contact of the phosphine with the pyrolysis furnace inner surfaces.

One method of pretreatment is to soak the pyrolysis furnace with a phosphine-containing formulation prior to processing EDC feed. Another method of pretreatment is to use a known chemical vapor deposition (CVD) method to lay the phosphine on the inner surfaces of the pyrolysis furnace.

For continuous or intermittent treatment, the phosphine is added into the pyrolysis furnace during the presence of EDC feed. The recommended addition rate for the phosphine ranges from about 1 to about 5000 part per million (ppm) based on the EDC feed rate by weight, preferably from about 10 to about 1000 ppm, and most preferably from about 20 to about 200 ppm.

For continuous and intermittent treatment, the phosphine can be injected at any location prior to the pyrolysis furnace. These injection points, can include, but are not limited to, the inlet to the convection section or the crossover section between the convection section and the radiant section or at the front of the TLE.

The following examples are presented to be illustrative of the present invention and to teach one of ordinary skill how to make and use the invention. These examples are not intended to limit the invention or its protection in any way.

EXAMPLES

A bench scale pyrolysis furnace was used to simulate the industrial pyrolysis operation. Also used were a microbalance and a gas chromatograph, allowed the monitoring of coke formation and pyrolysis product distribution and conversion.

The bench scale pyrolysis furnace consisted of a coiled preheater (simulating the convection section), a tubular pyrolysis reactor (radiant section), an electronic microbalance and a gas chromatograph (GC). The preheater was made out of Incoloy 800, a Ni—Cr—Fe alloy, and the pyrolysis reactor was made out of quartz. Both the preheater and the pyrolysis furnace were heated using electrical heaters. A metal alloy specimen of Incoloy 800H, a Ni—Cr—Fe alloy, was suspended in the radiant section of the furnace reactor, and its weight was constantly recorded by the microbalance.

During operation of the pyrolysis furnace (cracking EDC) coke formed on the metal specimen, and thus, any weight increase during the cracking operation was a measure of coke deposition on the metal coupon. The typical output from the microbalance was a plot of coke buildup vs. time on stream. Two pieces of information from the plot is the total coke accumulation during a cracking test and the coking rate at each individual moment. The coking rate is a measure of coke accumulation per unit time at a given moment, and it is measured by the slope of the coke buildup-time curve at that moment.

In addition to the microbalance analysis, the effluent from the exit of the pyrolysis furnace was sampled periodically for GC analysis. EDC conversion and VC yield were obtained based on the GC analysis. EDC conversion was defined as the percentage of the EDC feed being consumed through the pyrolysis furnace, and the VC yield was the percentage of the EDC feed which was converted to VC.

During a cracking operation, EDC feed was pumped into the pyrolysis furnace at a rate of about 11 cc/hour. The EDC feed was evaporated in the entrance part of the preheater, and heated to about 400° C. through the preheater. The heated EDC was then sent to the pyrolysis reactor for cracking reaction. The pyrolysis temperature was measured at the outside of the pyrolysis reactor and in the isothermal region of the electrical heater. During a cracking experiment, the temperature was controlled at 580° C. at which the EDC conversion was around 65%. The cracking reaction was carried out under atmospheric pressure. The residence time of the EDC feed in the pyrolysis reactor was estimated around 3 seconds. A typical cracking experiment lasted from about 2 to about 4 hours. The coke formation during a cracking experiment was measured by the quantity of the coke formed on the metal specimen and the coking rate after the coke formation reached a steady state.

The decoke operation was carried out at 550° C. under a continuous flow of a mixture of air, nitrogen and helium. The decoke lasted from 2 to 14 hours, and most of the coke was removed during the first hour of decoke.

Cracking experiments were conducted without any phosphine treatment to secure a "baseline" pattern for coke formation. In the cracking experiments without any phosphine treatment, it was observed that coke formation was very low on a fresh metal alloy, and a steady increase in coke formation was seen when the metal alloy specimen went through cracking-decoking cycles. After a certain number of the cracking-decoking cycles, the coke formation on the metal specimen took a sudden upturn, indicating a breakdown of intrinsic surface protection against coke formation, and thereafter, the metal specimen maintained the high coking activity.

In conducting the method of the instant claimed invention, all the metal alloy specimen were conditioned through numerous cracking-decoking cycles until the high coking activity was obtained, and sustained, and then, such conditioned metal specimen were used in collecting coke formation data.

The effectiveness of a phosphine coke inhibitor was measured by how much reduction in coke formation was obtained when treating a conditioned metal specimen with the phosphine. In a phosphine treated cracking experiment, a selected phosphine was premixed in EDC feed at a dosage of around 200 ppm, based on the weight of EDC, and the phosphine-containing EDC feed was then used as feed during the cracking experiment.

Table 1 lists the phosphines, which have been tested in the cracking experiments.

TABLE 1

| ADDITIVES | LABELS |
|---|---|
| Tributyl phosphine | TBuP |
| triphenyl phosphine | TPP |

Figure 2:
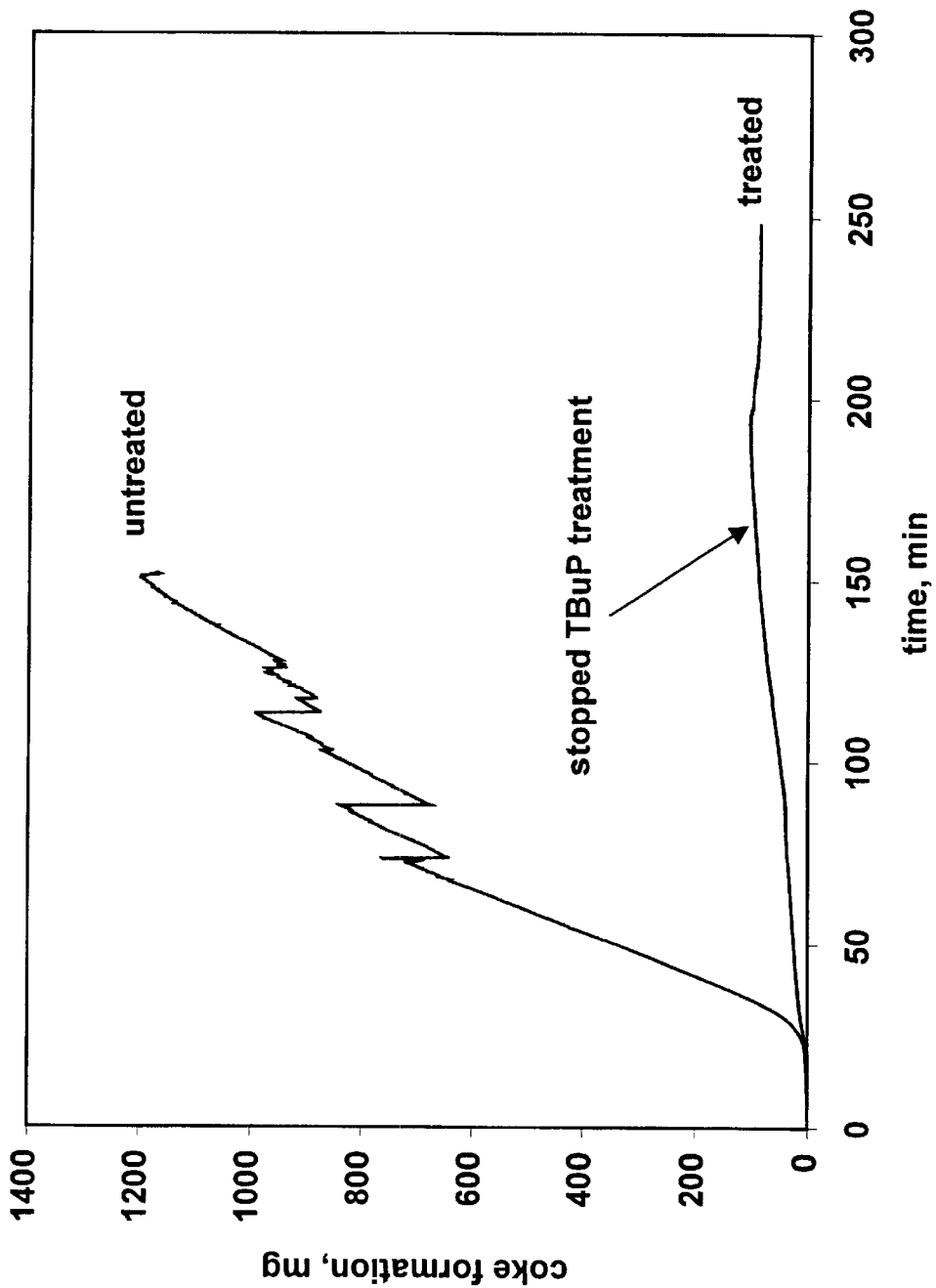
FIG. 2 is a graph illustrating the effectiveness of tributyl phosphine (TBuP) in inhibiting coke formation in comparison with an untreated run.

FIGS. 1–2 show the coke formation with TPP and TBuP treatment in comparison with an untreated. Clearly, both phosphine compounds are effective inhibitors for coke formation.

It was found that not all phosphorous containing compounds are effective in the reduction of coke formation in an EDC-VC pyrolysis furnace. Triphenyl phosphate, triphenyl phosphine oxide, dioctyl phenyl phosphonate and ethylhexyl ethylhexyl phosphonate were tested to see if it they were effective reducers of coke formation in an EDC-VC pyrolysis furnace. None of these phosphorous containing compounds were found to have any reduction effect on coke formation.

The effectiveness of the phosphine as coke inhibitor was also demonstrated in stabilizing EDC conversion and VC yield. It was observed that the acceleration in coke formation on a conditioned coupon was accompanied by a runaway EDC conversion and a deterioration in VC yield. With a phosphine treatment, both EDC conversion and VC yield held fairly steady during a cracking operation.

Figure 3:
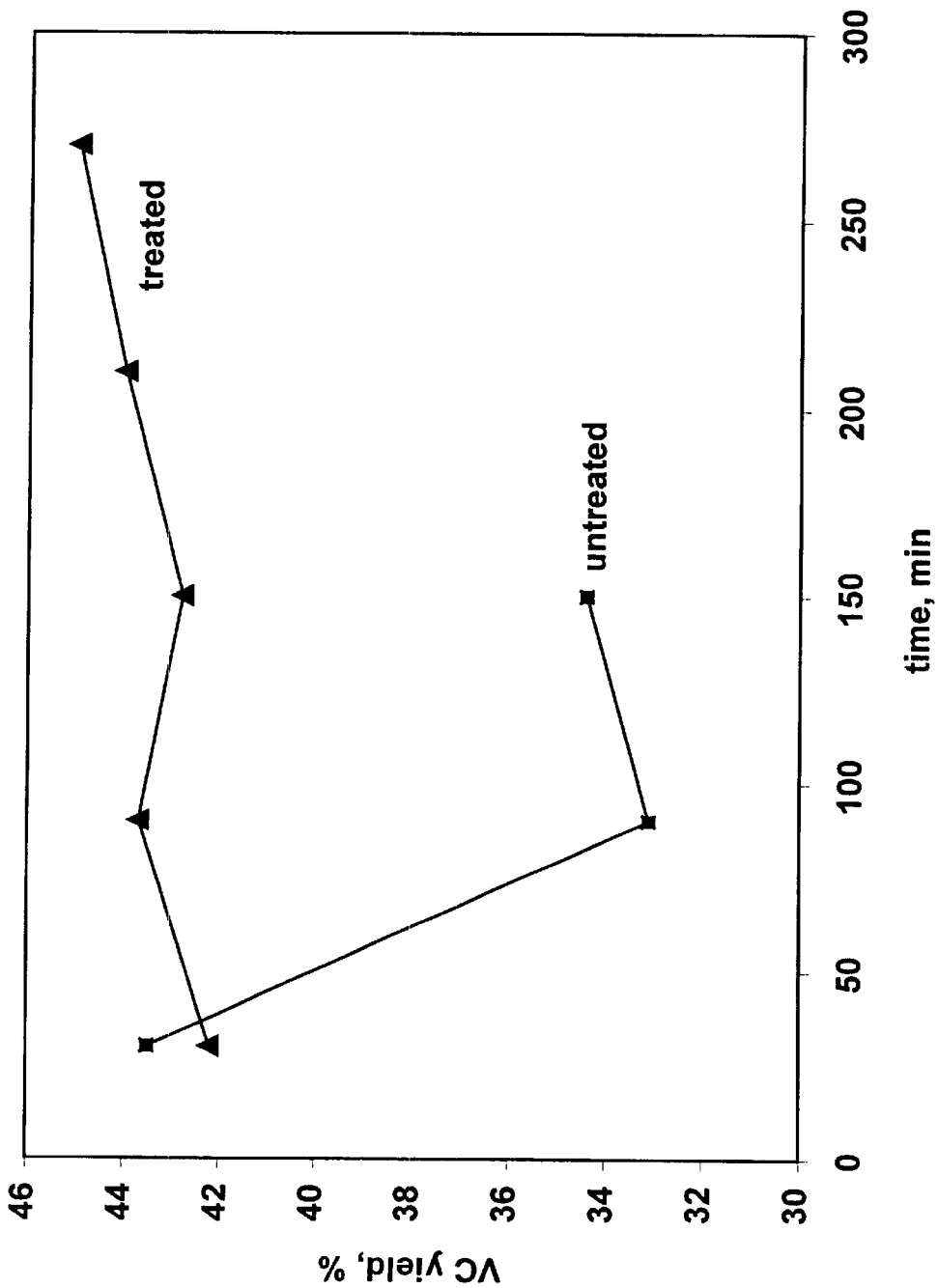
FIG. 3 is a graph illustrating the effectiveness of tributyl phosphine (TBUP) in stabilizing VC yield in comparison with an untreated run.

FIG. 3 shows the VC yield obtained during the runs given in FIG. 2 (treated with tributyl phosphine in comparison to an untreated run). As the figures indicated, for an untreated run, the sharp increase in coke formation was accompanied by a sharp decline in VC yield, while for a treated run, VC yield held steady during the whole run.

It is believed, without intending to be bound thereby, that the phosphine treatment functions to prevent the breakdown of a surface protective layer on the pyrolysis furnace walls, and with an intact surface protective layer, the formation of undesired catalytic sites is reduced. With a reduction in undesired catalytic sites, the runaway EDC conversion and deterioration in VC yield is avoided.

The specific examples herein disclosed are to be considered as being primarily illustrative. Various changes beyond those described will, no doubt, occur to those skilled in the art; such changes are to be understood as forming a part of this invention insofar as they fall within the spirit and scope of the appended claims.

What is claimed is:

1. A method of reducing the formation of coke deposits on the heat transfer surfaces of an ethylene dichloride to vinyl chloride pyrolysis furnace comprising exposing said heat transfer surfaces of said pyrolysis furnace to a phosphine selected from the group consisting of phosphines with the general formula:

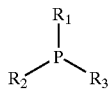

wherein $R_1$, $R_2$ and $R_3$ are selected from the group consisting of hydrogen, chlorine, alkyl, aryl, alkylaryl and arylalkyl, wherein $R_1$, $R_2$ and $R_3$ can be the same or different.

2. The method of claim 1 in which $R_1$, $R_2$ and $R_3$ are all the same.

3. The method of claim 1 in which said phosphine is selected from the group consisting of phosphorous trichloride, triphenyl phosphine, tri-n-butyl phosphine, tri-n-octyl phosphine, tridodecyl phosphine, tricyclohexyl phosphine, tribenzyl phosphine, tris(p-tolyl)phosphine, tris (1-naphthyl)phosphine, tris(anthracenyl)phosphine, tris(3-chlorophenyl)phosphine and tris(2-methoxyphenyl) phosphine.

4. The method of claim 1 wherein said phosphine is added continuously or intermittently to a ethylene dichloride feed which is then added to said pyrolysis furnace.

5. The method of claim 4 wherein said ethylene dichloride feed to said pyrolysis furnace is treated with from about 1 ppm to about 5000 ppm of said phosphine based on the weight of said ethylene dichloride feed.

6. The method of claim 4 wherein said phosphine is added to said pyrolysis furnace at a location prior to the radiant section of the pyrolysis furnace.

7. The method of claim 1 wherein said phosphine is blended with solvents or conversion boosters and then this blend is added to said pyrolysis furnace.

8. The method of claim 1 wherein said heat transfer surfaces are treated with said phosphine prior to processing of ethylene dichloride feed.

9. The method of claim 8 wherein said heat transfer surfaces are treated with said phosphine for from about 30 minutes to about two days.

10. The method of claim 8 wherein said phosphine is applied to said heat transfer surfaces by a method selected from the group consisting of spraying, soaking, painting, flushing and chemical vapor deposition.

* * * * *